United States Patent [19]

Rector et al.

[11] Patent Number: 4,870,082

[45] Date of Patent: Sep. 26, 1989

[54] ANTHELMINTIC QUINOLINYL ACYLHYDRAZONES, METHOD OF USE AND COMPOSITIONS

[75] Inventors: Douglas L. Rector, Kalamazoo; George A. Conder, Richland; Sylvester D. Folz, Kalamazoo, all of Mich.

[73] Assignee: The Upjohn Company, Kalamazoo, Mich.

[21] Appl. No.: 938,202

[22] PCT Filed: Apr. 7, 1986

[86] PCT No.: PCT/US86/00714

§ 371 Date: Nov. 24, 1986

§ 102(e) Date: Nov. 24, 1986

[87] PCT Pub. No.: WO86/05982

PCT Pub. Date: Oct. 23, 1986

[51] Int. Cl.$^4$ .............. A61K 31/47; C07D 401/12; C07D 215/50; C07D 215/54

[52] U.S. Cl. .............. 514/311; 546/153; 546/176; 546/122; 544/235; 544/238; 544/283; 544/333; 544/349; 544/405; 514/247; 514/253; 514/255; 514/256; 514/259; 514/300

[58] Field of Search .............. 546/176, 153, 122; 514/311, 247, 253, 255, 256, 259, 300; 544/238, 283, 333, 235, 349, 405

[56] References Cited

U.S. PATENT DOCUMENTS 3,136,769 6/1964 Werbel et al. .............. 546/153

FOREIGN PATENT DOCUMENTS 0139259 12/1979 German Democratic Rep. .............. 546/176

OTHER PUBLICATIONS

Capitan et al, Chem. Abstrs. 84, 11787x (1976).
Chem. Abstr. 65, 37f (1966).
Mahishi, B. et al, "Chlorophenoxyacetic Acids & Their Derivatives as Tuberculostats", J. Indian. Chem. Soc., 42 (2), pp. 67–74 (1965).
Chem. Abstr. 62, 16654g (1965).
Fjikawa, F. et al, Yakugaku Zasshi, 90, pp. 78–82 (1970).
Chem. Abstr. 72, 110952F (1970).
Sukhova, N. M., Sprunka, I., Lidaka, M. & Zidermane, A., Khim-Farm. Zh. 16, pp. 169–173 (1982).
Chem. Abstr. 96, 199484w (1984).
Frank, R. L. & Weatherbee, C., J. Am. Chem. Soc., 70, pp. 3482–3483 (1948).
Ogata, N. & Kano, H., Chem. Pharm. Bull. (Tokyo), 11, p. 32 (1963).
Grammaticakis, P., Compt. Rend. 248, pp. 3719–3721 (1959).
Chem. Abstr. 21153f (1959).
Bobarenic B. et al, Glasnik Hemicara & Technologia BiH, Sarajivo, 13/14. pp. 47–50 (1965).

Primary Examiner—David B. Springer
Attorney, Agent, or Firm—William G. Jameson

[57] ABSTRACT

This invention concerns a process for killing internal parasites, especially nematodes and cestodes affecting warm blooded animals such as sheep, cattle, swine, goats, dogs, cats, horses and humans as well as poultry by administering an effective amount of a compound of the Formula I:

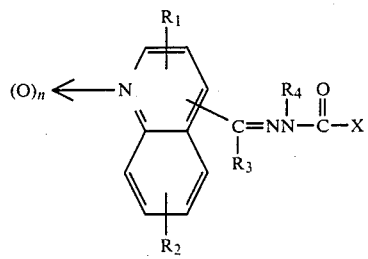

Certain of the compounds of Formula I are novel and in further embodiments of the invention provide novel compounds and compositions for use in the process of the invention. The compounds are readily prepared by conventional chemical reactions.

19 Claims, No Drawings

ANTHELMINTIC QUINOLINYL ACYLHYDRAZONES, METHOD OF USE AND COMPOSITIONS

This application is a continuation-in-part of Ser. No. 722,104, filed Apr. 11, 1985, now abandoned.

SUMMARY OF THE INVENTION

This invention pertains to a new method for killing and controlling worms (Helminths), and new formulations for killing and controlling worms in animals, and new chemical compounds. The invention is more particularly directed to a new method for killing and controlling parasitic worms in animals with certain quinolinyl acylhydrazones, to new anthelmintic formulations comprising the same, and to new quinolinyl acylhydrazones.

The anthelmintic quinolinyl acylhydrazones have the general structural formula I.

BACKGROUND OF THE INVENTION

The diseases or groups of diseases described generally as helminthiasis are due to infection of the animal with parasitic worms known as helminths. Helminthiasis and helminthosis are prevalent and may lead to serious economic problems in valuable domestic warm-blooded animals such as sheep, swine, cattle, goats, dogs, cats, horses, poultry; and man. Among the helminths, the groups of worms known as nematodes, trematodes and cestodes cause widespread and oftentimes serious infections in various species of animals including man. The most common genera of nematodes, trematodes and cestodes infecting the animals referred to above are Dictyocaulus, Haemonchus, Trichostrongylus, Ostertagia, Nematodirus, Cooperia, Bunostomum, Oesophagostomum, Chabertia, Strongyloides, Trichuris, Fasciola, Dicrocoelium, Enterobius, Ascaris, Toxascaris, Toxocara, Ascaridia, Capillaria, Heterakis, Ancylostoma, Uncinaria, Dirofilaria, Onchocerca, Taenia, Moniezia, Dipylidium, Metastrongylus, Triodontophorus, Macracanthorhynchus, Hyostrongylus, and Strongylus. Some of these genera attack primarily the intestinal tract while others, inhabit the stomach, lungs, liver and subcutaneous tissues. The parasitic infections causing helminthiasis and helminthosis lead to anemia, malnutrition, weakness, weight loss, unthriftiness, severe damage to the gastrointestinal tract wall and, if left to run their course, may result in death of the infected animals.

The anthelmintic activity of quinolinyl acylhydrazones has not been previously reported.

DETAILED DESCRIPTION OF THE INVENTION

The quinolinyl acylhydrazones of the invention, including hydrates or pharmaceutically acceptable salts thereof, are represented by Formula I wherein X is (a) hydrogen; (b) $C_1$–$C_{10}$ alkyl; (c) $C_2$–$C_6$ akenyl; (d) $C_2$–$C_6$ alkynyl; (e) cyclo($C_3$–$C_{10}$)alkyl optionally substituted with one, 2 or 3 $C_1$–$C_4$ alkyl, $C_2$–$C_4$ alkenyl, $C_1$–$C_4$ alkoxy, trifluoromethyl, or halo; (f) pyrrolidinyl; (g) piperidinyl; (h) 1-methylpyrrolidinyl; (i) 1-methylpiperidinyl; (j) $C_2$–$C_6$ alkoxyalkyl; (k) cyclo($C_3$–$C_{10}$)alkyl($C_1$–$C_4$)alkyl; (m) phenoxy($C_1$–$C_4$)alkyl optionally substituted with $C_1$–$C_4$ alkyl, $C_1$–$C_4$ alkoxy, halo, or trifluoromethyl; (n) uredio($C_1$–$C_4$)alkyl; (o) $C_2$–$C_6$ alkoxy; (p) diphenylmethoxy; (s) benzyloxy optionally substituted with one, 2 or 3 $C_1$–$C_4$ alkyl, $C_1$–$C_4$ alkoxy, halo, or trifluoromethyl; (t) heteroaromatic optionally substituted with one, 2 or 3 $C_1$–$C_4$ alkyl, $C_1$–$C_3$ alkoxy, halo, $C_1$–$C_3$ alkylthio, or trifluoromethyl; (u) phenyl optionally substituted with one, 2 or 3 $C_1$–$C_4$ alkyl, halo, hydroxy, trifluoromethyl, $C_2$–$C_6$ dialkylamino, $C_1$–$C_3$ alkylthio or nitro; or (v) phenyl optionally substituted with the divalent $C_1$–$C_2$ alkylenedioxy;

wherein $R_1$ and $R_2$, being the same or different, are hydrogen; hydroxy $C_1$–$C_4$ alkyl; $C_1$–$C_3$ alkoxy; $C_1$–$C_3$ alkylthio; halo or trifluoromethyl;

wherein $R_3$ is hydrogen; $C_1$–$C_4$ alkyl; cyclo($C_3$–$C_6$)alkyl optionally substituted with one, 2 or 3 $C_1$–$C_3$ alkyl, preferably cyclo($C_3$–$C_5$)alkyl optionally substituted; phenyl optionally substituted with one, 2 or 3 $C_1$–$C_4$ alkyl, halo, trifluoromethyl, or $C_1$–$C_3$ alkoxy; phenyl($C_1$–$C_3$)alkyl optionally substituted with one, 2 or 3 $C_1$–$C_4$ alkyl, halo, trifluoromethyl, or $C_1$–$C_3$ alkoxy; or 1,3-dioxacyclohexan-5-yl;

wherein $R_4$ is hydrogen; $C_1$–$C_2$ alkyl; cyclo($C_3$–$C_6$)alkyl optionally substituted with one, 2 or 3 $C_1$–$C_3$ alkyl, preferably cyclo($C_3$–$C_5$)alkyl optionally substituted; phenyl optionally substituted with one, 2 or 3 $C_1$–$C_4$ alkyl, halo, trifluoromethyl, or $C_1$–$C_3$ alkoxy; phenyl($C_1$–$C_3$)alkyl optionally substituted with one, 2 or 3 $C_1$–$C_4$ alkyl, halo, trifluoromethyl, or $C_1$–$C_3$ alkoxy;

wherein n is zero or one;

with the proviso that $R_1$, $R_2$, and $R_3$ are each hydrogen and X is 4-(1,1-dimethylethyl)phenyl only when the compound is not a 2- or 3-quinolinyl acylhydrazone;

with the proviso that $R_1$, $R_2$ and $R_3$ are each hydrogen and X is hydrogen or methyl only when the compound is not a 4-quinolinyl; and X is 2-methylphenyl only when the compound is not a 3-quinolinyl.

$C_-$–$C_-$ means the carbon content of various hydrocarbon-containing moieties is indicated by a prefix designating the minimum and maximum number of carbon atoms in the moiety. Thus ($C_1$–$C_3$) alkyl refers to alkyl of one to 3 carbon atoms, inclusive or methyl, ethyl, propyl, and isopropyl.

Halogen atom (halo) refers to a bromo, chloro, iodo or fluoro atom.

Heteroaromatic refers to an aromatic heterocycle of 5 to 10 members, containing one or two heteroatoms selected from the group consisting of oxygen, nitrogen or sulfur and includes quinoline, pyrrole, indole, benzofuran, benzothiophene, quinazoline, quinoxaline, imidazole, pyrazole, oxazole, isoxazole, thiazole, isothiazole, pyridazine, pyrimidine, pyrazine, benzimidazole, benzothiazole, benzoxazole, pyridine, thiophene or furan, as well as the N-oxides, hydrates and pharmaceutically acceptable salts thereof.

Pharmaceutically acceptable refers to those properties and/or substances which are acceptable to the patient from a pharmacologically-toxicological point of view and to the manufacturing pharmaceutical chemist from a physical-chemical point of view regarding composition, formulation, stability, patient acceptance and bioavailability.

Examples of $C_1$–$C_4$ alkyl are methyl, ethyl, propyl, butyl and isomeric forms thereof. Examples of $C_1$–$C_3$ alkoxy are methoxy, ethoxy, propoxy and isomeric forms thereof. Examples of phenoxy substituted with one, 2 or 3 $C_1$–$C_4$ alkyl are (o-, m-, or p-)tolyl, (o-, m-, or p-)ethylphenyl, p-tert-butylphenyl, 2,5-dimethylphenyl, 2,6-dimethylphenyl, 2,4-dimethylphenyl, (2,3,4-, 2,3,5-, 2,3,6-, 2,4,6- or 2,4,5-)trimethylphenyl.

Examples of $C_2$-$C_6$ dialkylamino are dimethylamino, diethylamino, methylethylamino, dipropylamino and ethylpropylamino.

Examples of phenyl($C_1$-$C_3$)alkyl are benzyl, phenylethyl and phenylpropyl. Examples of phenyl($C_1$-$C_3$)alkyl substituted with one, 2 or 3 $C_1$-$C_4$ alkoxy, halo or trifluoromethyl include 4-chlorobenzyl, 2-chlorophenylethyl, p-tolylethyl, 2-methylbenzyl, 4-methoxybenzyl. Examples of $C_1$-$C_3$ alkylthio include methylthio, ethylthio, and n-propylthio.

Examples of substituted cyclo($C_3$-$C_{10}$)alkyl are chrysanthemyl, 1-methylcyclopropyl and 2-methylcyclopropyl. Examples of cyclo($C_3$-$C_{10}$)alkyl($C_1$-$C_4$)alkyl are 2-cyclohexylethyl and cyclohexylmethyl. An example of substituted cyclo($C_3$-$C_6$)alkyloxy is menthyl.

Preferred quinolinyl acylhydrazones of Formula I are 3-quinolinyl acylhydrazones or 4-quinolinyl acylhydrazones; most preferably 4-quinolinyl acylhydrazones.

$R_1$ can be on either the A ring (the nitrogen containing ring of quinolinyl) or the B ring (the benzo moiety of quinolinyl). $R_2$ can only be on the B ring.

Preferred $R_1$ and $R_2$ include hydrogen, methyl or chloro. Preferred $R_3$ include hydrogen, methyl or ethyl. Preferred $R_4$ include hydrogen or methyl. Preferred X are phenyl, ethoxy or nicotinyl.

One embodiment of this invention includes, of course, the anthelmintic use and anthelmintic compositions of compounds of Formula I, hydrates thereof or pharmaceutically acceptable salts thereof.

Another embodiment of this invention are the novel compounds of Formula I, hydrates thereof of pharmaceutically acceptable salts thereof.

Another embodiment of this invention are the novel compounds of Formula I, the hydrates thereof or pharmaceutically acceptable salts thereof where X is phenyl, 3-methylphenyl, ethoxy or nicotinyl; preferably phenyl, ethoxy or nicotinyl.

Another embodiment of this invention are the compounds of Formula I, the hydrates thereof or pharmaceutically acceptable salts thereof where X is phenyl and at least one member of the group consisting of $R_1$, $R_2$, $R_3$ or $R_4$ is other than hydrogen.

Among the quinolinyl acylhydrazones of Formula I:
benzoic acid (2-quinolinylmethylene)hydrazide,
benzoic acid (4-quinolinylmethylene)hydrazide,
acetic acid (2-quinolinylmethylene)hydrazide,
acetic acid (4-quinolinylmethylene)hydrazide,
isonicotinic acid (4-quinolinylmethylene)hydrazide,
isonicotinic acid (2-quinolinylmethylene)hydrazide,
2,4,5-trichlorophenoxyacetic acid (2-quinolinylmethylene)hydrazide,
2,4-dichlorophenoxyacetic acid (2-quinolinylmethylene)hydrazide,
4-chlorophenoxyacetic acid (2-quinolinylmethylene)hydrazide, and
2-hydroxy-4-bromobenzoic acid (8-hydroxy-2-quinolinylmethylene)hydrazide are known.

See P. Grammaticakis, Compt. rend. 248, 3719–21 (1959) or Chem. Abstr. 21153f (1959); B. Bobarenic, M. Dezelu and V. Jovanaic, Glasnik Hemicara and Technologia BiH, Sarajivo, 13/14, 47–50 (1965) or Chem. Abstr. 65, 37f; N. B. Mahishi, B. H. Iyer and M. Sirisi, J. Indian Chem. Soc. 42 (2), 67–74 (1965) or Chem. Abstr. 62, 16654g; F. Fjikawa, et al., Yakugaku Zasshi 90, 78–82 (1970) or Chem. Abstr. 72, 110952f; and M. N. Sukhova, I. Sprunka, M. Lidoka and A. Zidermane, Khim-Farm. Zh. 16, 169–73 (1982) or Chem. Abstr. 96, 19948w.

The quinolinyl acylhydrazones of this invention (Formula I) are readily prepared by reacting the appropriate quinolyl ketone (II) with the acylhydrazide/carbazate (III) (Chart A, Scheme A) or by heating the quinolyl ketone (II) with the appropriate hydrazine (IV) to form the hydrazone intermediate (V) which is then acylated with the halide or anhydride (VI) to form the quinolinyl acylhydrazone (I) (Chart A, Scheme B).

The quinolinyl acylhydrazone N-oxides (formula I where n=1) are generally prepared by first oxidizing the quinolyl ketone (II) to furnish the quinolyl ketone n-oxide (VII) (Scheme C). The ketone VII is then reacted with the appropriate acylhydrazide or carbazate (III) to give the quinolinyl acylhydrazone N-oxide (I) or alternatively the quinolinylacylhydrazone (I) is formed by first reacting the ketone VII with a hydrazine IV to form hydrazone intermediate N-oxide VIII which in the final step is acylated with the halide VI to furnish the quinolinyl acylhydrazone N-oxide I.

The reaction is carried out in the presence of a suitable solvent, for example, water, alcohols, ethers, halogenated hydrocarbons, hydrocarbons and include methanol, ethanol, isopropanol, propanol, hexane, tetrahydrofuran, dioxane, methylene chloride, perferably ethanol. A catalyst such as glacial acetic acid, hydrochloric acid, sulfuric acid or p-toluenesulfonic acid can be utilized in Scheme A to enhance the yield/rate of the reaction, particularly when $R_3$ is alkyl of 3 or more atoms, arylalkyl or aryl. The reaction V→I of Scheme B is carried out in the presence of a suitable base such as a tertiary amine, for example, triethylamine or preferably, pyridine. The base may also be the solvent.

The desired N-oxide is prepared by oxidizing the appropriate ketone using a peracid such as perbenzoic, m-chloroperbenzoic, performic, peracetic or generating the peracid in situ preferably with hydrogen peroxide/acetic acid to furnish the quinolyl ketone N-oxide which is reacted with the appropriate hydrazide or carbazate (Chart A, Scheme C).

The starting compounds are known or can be readily prepared by known methods. R. L. Frank and C. Weatherbee, J. Am. Chem. Soc., 70, 3482–3 (1948); N. B. Mahishi, et al., J. Indian Chem. Soc., 42, 67–74 (1965) and M. Ogata and H. Kano, Chem. Pharm. Bull (Tokyo), 11, 32 (1963).

The following detailed examples/procedures describe how to prepare various quinolinyl acylhydrazones of the invention and are to be construed as merely illustrative, and not limitations of the proceeding disclosure in any way whatsoever. Those skilled in the art will promptly recognize appropriate variations from the procedures both as to reactants as well as to reaction conditions and techniques.

Procedure 1

Preparation of butyric acid (4-quinolinylmethylene)hydrazide, Compound 1

A mixture of 7.85 gm (0.05 mole) of 4-quinolinecarboxaldehyde, 5.11 gm (0.05 mole) of butyric acid hydrazide and 100 ml of ethanol is refluxed 4 hr. The reaction mixture is diluted with water and cooled to room temperature. The mixture is chilled. The solid that separates is collected, washed with water and dried to give 10.3 gm of the title compound, having a melting point of 130.4° C.

Calcd: C, 69.69; H, 6.27; N, 17.41. Found: C, 69.58; H, 6.22; N, 17.12.

Procedure 2

Preparation of 3-methylbenzoic acid (2-quinolinylmethyl-ene)hydrazide, Compound 4

A mixture of 3.3 gm (0.021 mole) of 2-quinolinecarboxaldehyde, 3.15 gm (0.021 mole) of m-toluic acid hydrazide and 150 ml of absolute ethanol is refluxed 10 hr. The hot solution is filtered then diluted with water until cloudy. The mixture is cooled to room temperature and then chilled. The solid is collected to give 2.2 gm (36%) of the title compound having a melting point of 187.5°–188° C. after recrystallizing from methylene chloride/diethyl ether.

Calcd: C, 74.72; H, 5.23; N, 14.52. Found: C, 74.58; H, 5.15; N, 14.84.

The title compound is remade with a scale-up of 9x using the above process to give 26.0 gm (47%); 187.1° C.

Calcd: C, 74,72; H, 5.23; N, 14.52. Found: C, 73.73; H, 5.26; N, 14.54.

Procedure 3

Preparation of acetic acid (2-quinolinylmethylene)hydrazide, Compound 5

A mixture of 4.4 gm (0.028 mole) of 2-quinolinecarboxaldehyde, 2.07 gm (0.028 mole) of acetylhydrazide and 150 ml of methanol is refluxed 9.5 hr. The hot solution is filtered. The filtrate is cooled to room temperature and then chilled. The solid is collected to give 3.42 gm (57.3%) of the title compound having a melting point of 218°–219° C.

Calcd: C, 67.59; H, 5.20; N, 19.71. Found: C, 67.27; H, 5.19; N, 19.58.

Procedure 4

Preparation of ethyl (4-quinolinylmethylene)carbazate, Compound 6

A mixture of 4.72 gm (0.03 mole) of 4-quinolinecarboxaldehyde, 3.12 gm (0.03 mole) of ethylcarbazate and 100 ml of absolute ethanol is refluxed 9 hr. The solvent is evaporated. The solid is crystallized from ethyl acetate/Skellysolve B to give 3.82 gm (53%) of the title compound having a melting point of 161.2° C.

Calcd: C, 64.20; H, 5.35; N, 17.28. Found: C, 63.96; H, 5.49; N, 17.16.

Procedure 5

Preparation of nicotinic acid (4-quinolinylmethylene)hydrazide, Compound 7

A mixture of 7.86 gm (0.05 mole) of 4-quinolinecarboxaldehyde, 6.86 gm (0.05 mole) of nicotinic acid hydrazide and 100 ml of ethanol is refluxed 2 hr. The reaction mixture is cooled to room temperature. The solid which sepatates is collected, washed with water and dried; 14.4 gm (quantitative) to give the title compound; mp. 99.6° C. The product is recrystallized from ethanol to give 11.54 gm (83%) of the title compound, having a melting point of 192.7° C.

Calcd: C, 69.56; H, 4.38; N, 20.27. Found: C, 69.58; H, 4.68; N, 20.38.

Procedure 6

Preparation of benzoic acid (2-quinolinylmethylene)hydrazide, Compound 8

A mixture of 4.08 gm (0.03 mole) of benzhydrazide, 4.72 gm (0.03 mole) of 2-quinolinecarboxaldehyde and 100 ml of absolute ethanol is refluxed 4 hr. The hot solution is filtered and cooled slowly to room temperature. The mixture is chilled. The crystals which separate are collected, washed with ether and dried to give 4.06 gm (50%) of the title compound having a melting point of 170.7° C.

Calcd: C, 74.18; H, 4.73. Found: C, 73.96; H, 4.61.

Procedure 7

Preparation of 1,1-dimethylethyl(2-quinolinylmethylene)carbazate, Compound 17

A mixture of 3.46 gm (0.022 mole) of 2-quinolinecarboxaldehyde, 2.91 gm (0.022 mole) of tert-butylcarbazate and 150 ml of methanol is refluxed 8 hr. The solvent is evaporated in vacuo to give a solid. The crude product is slurried in diethyl ether/Skellysolve B and collected. Crystallizing from acetone/water gives 2.84 gm (48%) of title compound, having a melting point of 178°–179° C.

Calcd: C, 66.40; H, 6.32; N, 15.49. Found: C, 66.58; H, 6.19; N, 15.65.

Procedure 8

Preparation of 3-hydroxybenzoic acid (2-quinolinylmethylene)hydrazide, Compound 20

A mixture of 3.3 gm (0.021 mole) of 2-quinolinecarboxaldehyde, 3.20 gm (0.021 mole) of m-hydroxybenzhydrazide and 100 ml of methanol is refluxed for 8 hrs. The solvent is evaporated in vacuo to give a solid. The crude product is crystallized from ethanol/DMF/water to yield 3.43 gm (56%) of the title compound, having a melting point of >272° C. (decomp.).

Calcd: C, 70.09; H, 4.50; N, 14.42. Found: C, 69.57; H, 4.51; N, 14.46.

Procedure 9

Preparation of ethyl (2-quinolinylmethylene)carbazate, Compound 21

A mixture of 3.93 gm (0.025 mole) of 2-quinolinecarboxaldehyde, 2.60 gm (0.025 mole) of ethylcarbazate and 100 ml of methanol is refluxed for 8 hrs. The hot solvent is evaporated in vacuo to give a solid. The crude product is crystallized from ethyl acetate/Skellysolve B to yield 1.19 gm (20%) of the title compound, having a melting point of 163°–165° C.

Calcd: C, 64.19; H, 5.39; N, 17.27. Found: C, 64.00; H, 5.59; N, 17.11.

Procedure 10

Preparation of 4-methoxybenzoic acid (2-quinolinylmethylene)hydrazide, Compound 22

A mixture of 3.14 gm (0.02 mole) of 2-quinolinecarboxaldehyde, 3.32 gm (0.02 mole) of 4-methoxybenzhydrazide and 100 ml of ethanol is refluxed for 9 hrs. The hot solution is filtered and cooled slowly to room temperature. The mixture is chilled. The crystals which separate are collected. The crude mixture is crystallized from ethyl acetate and recrystallized from tetrahydrofuran to yield 3.0 gm (49%) of title compound, having a melting point of 220°–222° C.

Calcd: C, 70.84; H, 4.95; N, 13.76. Found: C, 71.01; H, 5.09; N, 13.81.

The title compound is remade with a scale-up of 8x, using the above procedure to give 26.8 gm (55%) in two crops both of which melted at 217°–218° C.

Calcd: C, 70.84; H, 4.95; N, 13.76. Found: C, 70.78; H, 4.94; N, 13.92.

Procedure 11

Preparation of 3-nitrobenzoic acid (2-quinolinylmethylene)hydrazide, Compound 23

A mixture of 3.00 gm (0.019 mole) of 2-quinolinecarboxaldehyde, 3.44 gm (0.019 mole) of m-nitrobenzhydrazide and 100 ml of ethanol is refluxed for 9 hrs. The hot solution is filtered and cooled slowly to room temperature. The mixture is chilled. The crystals which separate are collected. The crude product is recrystallized from tetrahydrofuran to yield 3.04 gm (50%) of the title compound, having a melting point of 217°–218° C.

Calcd: C, 63.75; H, 3.78; N, 17.49. Found: C, 63.60; H, 3.82; N, 17.06.

The title compound is remade as the monohydrate employing the above process with a 10x scale-up to give 48.2 gm (79%) of product after recrystallization from ethanol/dimethylformamide/water; mp. 219°–220° C.

Calcd: C, 60.35; H, 4.17; N, 16.56; $H_2O$, 5.32. Found: C, 60.09; H, 4.18; N, 16.54; $H_2O$, 5.01.

Procedure 12

Preparation of 2-nitrobenzoic acid (2-quinolinylmethylene)hydrazide, Compound 24

A mixture of 2.99 gm (0.019 mole) of 2-quinolinecarboxaldehyde, 3.44 gm (0.019 mole) of o-nitrobenzhydrazide and 150 ml of absolute ethanol is refluxed 9 hrs. The solvent is evaporated in vacuo. The solid is crystallized from methanol to give 1.97 gm (32%) of title compound, having a melting point of 195°–196° C.

Calcd: C, 63.75; H, 3.78; N, 17.49. Found: C, 63.22; H, 3.69; N, 17.20.

Procedure 13

Preparation of methyl (4-quinolinylmethylene)carbazate, Compound 25

A mixture of 2.70 gm (0.03 mole) of methylcarbazate, 4.72 gm (0.03 mole) of 4-quinolinecarboxaldehyde and 100 ml of anhydrous methanol is refluxed 8.5 hr. The hot solution is filtered. The filtrate is diluted with water until cloudy. The mixture is cooled to room temperature then chilled. The crystals are collected, washed with ether and dried to give 5.88 gm (86%) of the title compound, having a melting point of 83.5° C.

The title compound is remade (as a monohydrate) using the above process at a 5x scale-up to give 30.56 gm (80%) of the product; mp. 89.3°.

Calcd: C, 58.30; H, 5.26; N, 17.00. Found: C, 58.82; H, 5.49; N, 17.01.

Procedure 14

Preparation 4-trifluoromethylbenzoic acid (4-quinolinylmethylene)hydrazide, Compound 26

To 7.86 gm (0.05 mole) of 4-quinolinecarboxaldehyde in absolute ethanol is added 10.21 gm (0.05 mole) of 4-trifluoromethylbenzyhdrazide. The mixture is refluxed 2 hrs. and cooled to room temperature. The solids are collected, washed with Skellysolve B and dried to give 15.13 gm of title compound, having a melting point of 239.9° C.

Calcd: C, 62.98; H, 3.52; N, 12.24. Found: C, 62.87; H, 3.59; N, 12.25.

Procedure 15

Preparation of 4-methoxybenzyl(4-quinolinylmethylene)carbazate, Compound 28

A mixture of 7.86 gm (0.05 mole) of 4-quinolinecarboxaldehyde, 9.81 gm (0.05 mole) of 4-methoxybenzylcarbazate, 15 drops of glacial acetic acid and 100 ml of ethanol is refluxed 4 hr. The reaction mixture is chilled. The solid which separates is collected, washed with cold ethanol and dried to give 15.68 gm (94%) of the title compound, having a melting point of 182.8° C.

Calcd: C, 68.05; H, 5.11; N, 12.52. Found: C, 67.75; H, 5.38; N, 12.60.

Procedure 16

Preparation of cyclobutanecarboxylic acid (4-quinolinylmethylene)hydrazide, Compound 29

A mixture of 7.86 gm (0.05 mole) of 4-quinolinecarboxyaldehyde, 5.70 gm (0.05 mole) of cyclobutanecarboxylic acid hydrazide, 15 drops of glacial acetic acid and 100 ml of ethanol is refluxed 10 hours. The solvent is evaporated to give an oil. The oil is worked with ethyl acetate and the mixture is evaporated in vacuo. The oil is re-worked with ethyl acetate two additional times to induce crystallization. The solid is collected, washed with Skellysolve B and dried to give 8.67 gm (68%) of title compound, having a melting point of 138.0° C.

Cacld: C, 71.13; H, 5.97; N, 16.58. Found: C, 71.17; H, 6.32; N, 16.80.

Procedure 17

Preparation of 4-chlorobenzoic acid (4-quinolinylmethylene)hydrazide, Compound 30

A mixture of 7.86 gm (0.05 mole) of 4-quinolinecarboxaldehyde, 8.53 gm (0.05 mole) of 4-chlorobenzhydrazide, 400 ml of ethanol and 100 ml of tetrahydrofuran is refluxed 2 hr. Thin layer chromatography of the reaction mixture establishes that the reaction is complete. The reaction mixture is concentrated to one-half the original volume and then cooled to room temperature. The solid which separates is collected, washed with ethanol and dried to give 13.18 gm (85%) of title compound, having a melting point of 232.6° C.

Calcd: C, 65.92; H, 3.90; Cl, 11.45; N, 13.56. Found: C, 65.56; H, 4.08; Cl, 11.41; N, 13.44.

The compounds prepared according to Procedures 1–17 are tabulated in Table A along with other illustrative compounds of the invention prepared following the general procedure indicated (Procedures 1–17) and making non-critical variations, except starting with the appropriate quinolyl ketone (II) and acylhydrazide/carbazate (III).

The quinolinyl acylhydrazones of this invention (Formula I) are effective against parasitic worms, particularly those of valuable domestic warm-blooded animals and more particularly helminth parasites in ovines (sheep) and bovines (cattle).

Observations in sheep experimentally infected with *Haemonchus contortus* in accordance with Procedure 1, generally confirm anthelmintic activity at 100 mg/kg of body weight upon oral and/or parenteral administration as set forth in Table I. Quinolinyl acylhydrazones which are toxic at 100 mg/kg are expected to exhibit anthelmintic activity at a lower non-toxic dose. Further observations in sheep naturally infected with various helminths also confirmed broad-spectrum anthelmintic activity of a quinolinyl acylhydrazone of this invention. See Procedure 2 and the results as set forth in Table II.

Procedure No. 1

In individual experiments all sheep are treated identically, however non-critical variations occur between experiments. All of the sheep used in this procedure are treated twice with levamisole hydrochloride orally at 8 mg/kg or once each with ivermectin parenterally at 200 µg/kg and levamisole hydrochloride orally at 8 mg/kg. The second treatment in each case is administered 4–7 days after the first treatment. Two weeks after the second treatment all sheep are inoculated per os with ~3,500 to ~7,500 infective larvae of H. contortus. Rectal fecal samples are taken from each sheep 26–41 days post-inoculation (PI), and these samples are examined for eggs of H. contortus using the McMaster counting chamber technique. All sheep harboring good infections of H. contortus are randomly allocated to a treatment group; those which do not exhibit suitable infections are dropped from the study. One-three days later on days 27–42 PI each sheep remaining in the study (excluding the nontreated controls) is treated with a test compound (orally or parenterally at 100 mg/kg unless indicated otherwise) or a standard (levamisole hydrochloride orally at 8 mg/kg) or is used as an untreated control. All sheep received food and water ad lib. throughout the experiment.

Prior to administration, all solid compounds are finely ground using a mortar and pestle. Oral compounds are suspended in 20–30 ml of sterile vehicle TM 98 (each ml contains: carboxymethylcellulose - 10 mg, polysorbate80 —4 mg, propylparaben - 0.42 mg) using a sonicator and administered along with a tap water wash via a stomach tube. The parenteral compounds are similarly suspended in 20–30 ml of the sterile vehicle and given by intraperitoneal injection using a 13 gauge, 2 inch needle and a 50 ml syringe. All test compounds are given to a single sheep/route of administration. Two or more sheep are treated with levamisole hydrochloride and five are used as nontreated controls. All animals are monitored for signs of toxicity following treatment.

The sheep are sacrificed 7–12 days after treatment (days 35–49 PI), and the abomasum is ligated and removed from each sheep. Each abomasum is longitudinally sectioned and rinsed into an 80 mesh sieve. Sieve contents are collected in individual containers and fixed in formol-alcohol. Later each sample is transferred to a 1000 or 2000 ml beaker and the volume brought to 400–1000 ml with tap water. The total number of worms in a 40–100 ml aliquot (10%) is determined. When no worms are found in the 10% aliquot, the entire sample is examined. Total worm number/sheep and percentage clearance for each treatment are calculated. Percentage clearance for a particular test compound in a given trial is determined according to the following formula:

Percentage Clearance (Test Compound) =

[(Mean number of worms recovered from nontreated control sheep - Number of worms recovered from treated sheep)/Mean number of worms recovered from nontreated control sheep] × 100.

Sheep which die within 24 hr following treatment are not examined for worms, while any that die between 24 hr post-treatment and necropsy are examined in an identical manner as that described above. The results of various trials are combined and reported in Table I as percentage clearance.

Procedure No. 2

Parasitized sheep are randomly assigned to groups of five animals based on parasitic burden, sex, and farm origin. Sheep are double eartagged, weighed, housed in a barn in community pens, fed hay supplemented with ½ lb corn/head/day. Water is given ad lib. Animals are allowed to acclimate for one-two weeks prior to treatment.

Each group of sheep receives a test compound either orally or parenterally at a dosage rate of 100 mg/kg. A group of sheep is treated with 8 mg/kg of levamisole hydrochloride and another group serves as an untreated control group. Orally administered compounds are suspended in 20–30 ml of sterile vehicle TM 98 (each ml contains: carboxymethylcellulose - 10 mg, polysorbate80 —4 mg, propylparaben - 0.42 mg) using a sonicator and administered along with a tap water was via a stomach tube. For parenteral administration, compounds are similarly suspended in 20–30 ml of the sterile vehicle and given by intraperitoneal injection using a 20 gauge, 1 inch needle and a 50 ml syringe. Following treatment, all animals are observed for signs of toxicity.

The number and classification of helminth eggs per gram of feces (e.p.g.) are determined for each sheep during the acclimation period and in some cases at necropsy. Egg counts are made using the McMaster counting chamber technique and rectal fecal samples. Animals dying during the 24 hours immediately following dosing are not subjected to necropsy. Sheep that die 1–6 days posttreatment are posted and complete worm counts performed. All remaining animals are sacrificed on days 7–8 posttreatment. Each sheep is euthanised and bled out prior to opening the abdominal cavity. Ligatures are placed at the reticuloomasal junction, the pyloric valve, and the ileo-cecal junction. The abomasum and small intestine are freed of fat and mesenteric attachments, longitudinally opened, and their contents placed in individual containers. The mucosal surface of each is washed with tap water, rubbed clean, and rinsed several times. Washings and ingesta for each organ are made up to 1 liter and a 10% aliquot in formalin is stored for later examination. The cecum, large intestine, and colon are freed of mesenteric attachments, each is longitudinally opened, and their contents washed, collected, and made up to 1 liter in 10% formalin. The entire sample is stored. All carcasses are incinerated.

Ten percent of the total contents collected from the abomasum and small intestine and the entire contents of the large intestine, cecum, and colon are examined under stereoscopic magnification (40X). All worms are identified to genus and in some instances species. Separate adult and larval counts are determined.

The mean percentage clearance against specific helminths in the test sheep is calculated by subtracting the mean number of helminths observed in the treated sheep at necropsy from the mean number observed in the nontreated controls at necropsy, dividing the remainder by the latter mean number and multiplying by 100. The mean percentage clearances against the various helminths identified in the test sheep are calculated. The results for a quinolinyl acylhydrazones of Formula I are set forth in Table II.

From an evaluation of the test results set forth in Tables I and II, it is clear that the quinolinyl acylhydrazones of this invention (Formula I) are broad-spectrum anthelmintic agents.

DETAILED DESCRIPTION (cont'd)

The quinolinyl acylhydrazones of Formula I can be used as the pure compounds or as mixtures of pure compounds but for practical reasons the compounds are preferably formulated as anthelmintic compositions and administered as a single or multiple dose, alone or in combination with other anthelmintics (e.g. avermectins, benzimidazoles, levamisole, praziquantel, etc.). For example, aqueous or oil suspensions can be administered orally, or the compounds can be formulated with a solid carrier for feeding. Furthermore, an oil suspension can be converted into an aqueous emulsion by mixing with water and injecting the emulsion intramuscularly, subcutaneously or into the peritoneal cavity. In addition, the active compound(s) can be administered topically to the animal in a conventional pour-on formulation.

Pure compounds, mixtures of the active compounds, or combinations thereof with a solid carrier can be administered in the animal's food, or administered in the form of tablets, pills, boluses, wafers, pastes, and other conventional unit dosage forms, as well as sustained release dosage forms which deliver the active compound over an extended period of days, weeks or months. All of these various forms of the active compounds of this invention can be prepared using physiologically acceptable carriers and known methods of formulation and manufacture.

Representative solid carriers conveniently available and satisfactory for physiologically acceptable, unit dosage formulations include corn starch, powdered lactose, powdered sucrose, talc, stearic acid, magnesium stearate, finely divided bentonite, and the like. The active agent can be mixed with a carrier in varying proportions from, for example, about 0.001 percent by weight in animal feed to about 90 or 95 percent or more in a pill or capsule. In the latter form, one might use no more carrier than sufficient to bind the particles of active compound.

In general, the compounds can be formulated in stable powders or granules for mixing in an amount of feed for a single feeding or enough feed for one day and thus obtain therapeutic efficacy without complication. It is the prepared and stored feeds or feed premixes that require care. A recommended practice is to coat a granular formulation to protect and preserve the active ingredient. A prepared hog-feed containing about 0.2 percent of the active compound will provide a dosage of about 100 mg per kg body weight for each 100 lb pig in its daily ration.

A solid diluent carrier need not be a homogeneous entity, but mixtures of different diluent carriers can include small proportions of adjuvants such as water; alcohols; protein solutions and suspensions like skimmed milk; edible oils; solutions, e.g., syrups; and organic adjuvants such as propylene glycols, sorbitol, glycerol, diethyl carbonate, and the like.

The solid carrier formulations of the inventions are conveniently prepared in unit dosage forms, to facilitate administration to animals. Accordingly, several large boluses (about 20 g weight) amounting to about 54 g of active compound would be required for a single dosage to a 900 lb horse at a dosage rate of 50 mg/kg of body weight. Similarly, a 60 lb lamb at a dosage rate of 100 mg/kg of body weight would require a pill, capsule, or bolus containing about 2.7 g of active compound. A small dog, on the other hand, weighing about 20 lbs. would require a total dosage of about 225 mg at a dosage rate of 25 mg/kg of body weight. The solid, unit dosage forms can be conveniently prepared in various sizes and concentrations of active ingredient, to accomodate treatment of the various sizes of animals that are parasitized by worms.

Liquid formulations can also be used. Representative liquid formulations include aqueous (including isotonic saline) suspensions, oil solutions and suspensions, and oil in water emulsions. Aqueous suspensions are obtained by dispersing the active compound in water, preferably including a suitable surface-active dispersing agent such as cationic, anionic, or non-ionic surface-active agents. Representative suitable ones are polyoxyalkylene derivatives of fatty alcohols and of sorbitan esters, and glycerol and sorbitan esters of fatty acids. Various dispersing or suspending agents can be included and representative ones are synthetic and natural gums, tragacanth, acacia, alginate, dextran, gelatin, sodium carboxymethylcellulose, methylcellulose, sodium polyvinylpyrrolidone, and the like. The proportion of the active compound in the aqueous suspensions of the invention can vary from about 1 percent to about 20 percent or more.

Oil solutions are prepared by mixing the active compound and an oil, e.g. an edible oil such as cottonseed oil, peanut oil, coconut oil, modified soybean oil, and sesame oil. Usually, solubility in oil will be limited and oil suspensions can be prepared by mixing additional finely divided compound in the oil.

Oil in water emulsions are prepared by mixing and dispersing an oil solution or suspension of the active compound in water preferably aided by surface-active agents and dispersing or suspending agents as indicated above.

In general, the formulations of this invention are administered to animals so as to achieve therapeutic or prophylactic levels of the active compound. At present, it is known that a dose of 100 mg/kg of body weight in sheep of a quinolinyl acylhydrazone of this invention will effectively combat a wide variety of parasites. Much lower effective dosages of various quinolinyl compounds are contemplated, e.g., in the range of 1 to 75 mg/kg of body weight.

In other animals, and for other kinds of parasitic worms, definitive dosages can be proposed. Contemplated are dosage rates of about 1 mg to about 800 mg/kg of body weight. A preferred, contemplated range of dosage rates is from about 5 mg to about 400 mg/kg of body weight. In this regard, it should be noted that the concentration of active compound in the formulation selected for administration is in many situations not critical. One can administer a larger quantity of a formulation having a relatively low concentration and achieve the same therapeutic or prophylactic dosage as a relatively small quantity of a relatively more concentrated formulation. More frequent small dosages will likewise give results comparable to one large dose. One can also administer a sustained release dosage system (protracted delivery formulation) so as to provide therapeutic and/or prophylactic dosage amounts over an extended period. Unit dosage forms in accordance with this invention can have anywhere from less than 1 mg to 500 g of active compound per unit.

Although the anthelmintic agents of this invention will find their primary use in the treatment and/or prevention of helminth parasitisms in domesticated animals such as sheep, cattle, horses, dogs, swine, goats and poultry, they are also effective in treatment that occurs in other warm blooded animals including man. The optimum amount to be employed for best results will, of course, depend upon the particular quinolinyl compound employed, species of animal to be treated, the regimen treatment and the type and severity of helminth infection. Generally good results are obtained with compounds of Formula I by the oral or parenteral route of administration of about 1 to 300 mg/kg of animal bodyweight (such total dose being given at one time, in a protracted manner or in divided doses over a short period of time such as 1–4 days). The technique for administering these materials to animals are known to those skilled in the veterinary and medical fields.

It is contemplated that the quinolinyl acylhydrazones of Formula I can be used to treat various helminth diseases in humans, including those caused by Ascaris, Enterobius, Ancylostoma, Trichuris, Strongyloides, Fasciola, Taenia, and/or Onchocerca or other filaria at a dose of from 1 mg/kg to 300 mg/kg of body weight upon oral and/or parenteral administration.

DEFINITIONS

The definitions and explanations below are for the terms as used throughout the entire patent application including both the specification and claims.

All temperatures are in degrees Celsius.

TLC refers to thin-layer chromatography.

Brine refers to an aqueous saturated sodium chloride solution.

When solvent pairs are used, the ratio of solvents used are volume/volume (v/v).

TABLE A

| C | a | n | $R_1$ | $R_2$ | $R_3$ | $R_4$ | X | m.p. (°C.) | P | H |
|---|---|---|---|---|---|---|---|---|---|---|
| 1 | 4 | 0 | H | H | H | H | $CH_3CH_2CH_2$ | 130.4 | 1 | — |
| 2 | 4 | 0 | H | H | H | H | $c-C_6H_{11}-CH_2CH_2$ | 149.5 | 1 | — |
| 3 | 4 | 0 | H | H | H | H | $i-C_3H_7$ | 150.1 | 1 | — |
| 4 | 2 | 0 | H | H | H | H | 3-$CH_3$Ph | 187.5-188 | 2 | — |
| 5 | 2 | 0 | H | H | H | H | $CH_3$ | 218-219 | 3 | — |
| 6 | 4 | 0 | H | H | H | H | $CH_3CH_2O$ | 161.2 | 4 | — |
| 7 | 4 | 0 | H | H | H | H | 3-pyridyl | 192.7 | 5 | — |
| 8 | 2 | 0 | H | H | H | H | Ph | 170.7 | 6 | — |
| 9 | 2 | 0 | H | H | H | H | 3-pyridyl | 136.0 | 6 | + |
| 10 | 4 | 0 | H | H | H | H | 3-pyridyl | 90.6 | 6 | + |
| 11 | 4 | 0 | H | H | H | H | Ph | 211.1 | 6 | — |
| 12 | 2 | 0 | H | H | H | H | $CH_2NHCONH_2$ | 217.0 | 6 | — |
| 13 | 4 | 0 | H | H | H | H | $PhCH_2O$ | 159.5 | 6 | — |
| 14 | 2 | 0 | H | H | H | H | 4-$CH_3CH_2O$Ph | 195-196 | 6 | — |
| 15 | 2 | 0 | H | H | H | H | 2-$CH_3$Ph | 209.0 | 6 | — |
| 16 | 4 | 0 | H | H | H | H | 2-thienyl | 213.2 | 6 | — |
| 17 | 2 | 0 | H | H | H | H | $t-C_4H_9O$ | 178-179 | 7 | — |
| 18 | 2 | 0 | H | H | H | H | 2-ClPh | 159-163 | 7 | — |
| 19 | 2 | 0 | H | H | H | H | 2-$CH_3O$Ph | 184-185 | 7 | — |
| 20 | 2 | 0 | H | H | H | H | 3-HOPh | >272d | 8 | — |
| 21 | 2 | 0 | H | H | H | H | $CH_3CH_2O$ | 163-165 | 9 | — |
| 22 | 2 | 0 | H | H | H | H | 4-$CH_3O$Ph | 220-222 | 10 | — |
| 23 | 2 | 0 | H | H | H | H | 3-$O_2N$Ph | 217-218 | 11 | — |
| 24 | 2 | 0 | H | H | H | H | 2-$O_2N$Ph | 195-196 | 12 | — |
| 25 | 4 | 0 | H | H | H | H | $CH_3O$ | 89.3 | 13 | — |
| 26 | 4 | 0 | H | H | H | H | 4-$CF_3$Ph | 239.9 | 14 | — |
| 27 | 4 | 0 | H | H | H | H | 2-furyl | 133.8 | 6 | — |
| 28 | 4 | 0 | H | H | H | H | 4-$CH_3O$Ph$CH_2O$ | 182.8 | 16 | — |
| 29 | 4 | 0 | H | H | H | H | $c-C_4H_7$ | 138.0 | 17 | — |
| 30 | 4 | 0 | H | H | H | H | 4-ClPh | 232.6 | 18 | — |
| 31 | 4 | 0 | H | H | H | H | $c-C_6H_{11}$ | 181.3 | 1 | — |
| 32 | 4 | 0 | H | H | H | H | 2-$CH_3$Ph | 221.2 | 6 | — |
| 33 | 4 | 0 | H | H | H | H | 3-$CH_3$Ph | 193.6 | 6 | — |
| 34 | 3 | 0 | H | H | H | H | 2-furyl | 232.7 | 14 | — |
| 35 | 4 | 0 | H | H | H | H | $CH_3CH_2$ | 150.4 | 1 | — |
| 36 | 4 | 0 | H | H | H | H | $t-C_4H_9O$ | 156.8 | 1 | — |
| 37 | 4 | 0 | H | H | H | H | 4-$t-C_4H_9$Ph | 221.2 | 6 | — |
| 38 | 3 | 0 | H | H | H | H | 4-$CH_3$Ph | 259.1 | 14 | — |
| 39 | 3 | 0 | H | H | H | H | $CH_3CH_2$ | 180.2 | 14 | — |
| 40 | 3 | 0 | H | H | H | H | 2-ClPh | 204.7 | 14 | — |
| 41 | 3 | 0 | H | H | H | H | $c-C_6H_{11}$ | 198.7 | 14 | — |
| 42 | 3 | 0 | H | H | H | H | 3-ClPh | 207.9 | 14 | — |
| 43 | 3 | 0 | H | H | H | H | $CH_3$ | 220.9 | 14 | — |
| 44 | 3 | 0 | H | H | H | H | 3-$CH_3$Ph | 219.3 | 14 | — |
| 45 | 3 | 0 | H | H | H | H | $t-C_4H_9O$ | 201.6 | 1 | — |
| 46 | 4 | 0 | H | H | H | H | 2-ClPh | 195.3 | 14 | — |
| 47 | 4 | 0 | H | H | H | H | 3-ClPh | 208.9 | 14 | — |
| 48 | 4 | 0 | H | H | H | H | 4-$CH_3$Ph | 208.3 | 6 | — |
| 49 | 4 | 0 | H | H | H | H | 2-Furyl | 133.8 | 7 | — |

The position (2-, 3- or 4-) of attachment (a) of the quinolinyl moiety is indicated in column "a".

TABLE I

| Compound | H. contortus % Clearance | |
|---|---|---|
| | P.O. | I.P. |
| 1 | * | N.T. |
| 2 | * | N.T. |
| 3 | * | N.T. |
| 4 | 53.3 | 29.8 |
| 5 | N.T. | N.T. |
| 6 | 82.9 | 61.2 |
| 7 | N.T. | N.T. |
| 8 | 33.0 | N.T. |
| 9 | 76.8 | N.T. |
| 10 | N.T. | N.T. |
| 11 | 96.8 | N.T. |
| 12 | 32.9 | 23.7-26.6 |
| 13 | N.T. | N.T. |
| 14 | 36.8 | 0 |
| 15 | 32.0 | 0 |
| 16 | 25.2 | 80.1 |
| 17 | N.T. | N.T. |
| 18 | N.T. | N.T. |
| 19 | N.T. | N.T. |
| 20 | 0 | 20.3 |
| 21 | N.T. | N.T. |
| 22 | 0 | 14.3 |
| 23 | 39.5 | 0 |
| 24 | N.T. | N.T. |
| 25 | 3.4 | N.T. |
| 26 | 40.2 | 29.0 |
| 27 | * | N.T. |
| 28 | * | N.T. |
| 29 | 99.8 | 88.4 |
| 30 | * | N.T. |
| 31 | * | N.T. |
| 32 | * | N.T. |
| 33 | * | N.T. |
| 34 | * | N.T. |
| 35 | * | N.T. |
| 36 | * | N.T. |
| 37 | * | N.T. |
| 38 | * | N.T. |
| 39 | 96.4 | N.T. |
| 40 | * | N.T. |
| 41 | 98.2 | N.T. |
| 42 | * | N.T. |
| 43 | 85.4 | N.T. |
| 44 | * | N.T. |
| 45 | * | N.T. |
| 46 | * | N.T. |
| 47 | * | N.T. |
| 48 | * | N.T. |
| 49 | * | N.T. |

N.T. = not tested
_-_, means the compound was tested two or more times and the extreme values reported (for example, 23.7-26.6)
I.P. = Intraperitoneal administration
P.O. = oral administration
*Tested, Data inconclusive (due to failure of untreated controls)

TABLE II

| | Percentage Clearance of Adult Worms by Genus or Species (100 mg/kg) | | | | | | |
|---|---|---|---|---|---|---|---|
| Cmp. # | Route | H. | Ost. | T.a. | T.c. | N. | Trich. | Oes. |
| 6 | Oral | 94.1 | 79.4 | 0 | 61.4 | 45.2 | 11.1 | 33.3 |

Definitions:
H. — Haemonchus
Ost. — Ostertagia
T.a. — Trichostrongylus axei
T.c. — Trichostrongylus colubriformis
N. — Nematodirus
Trich. — Trichuris
Oes. — Oesophagostomum

CHART A

Scheme A:

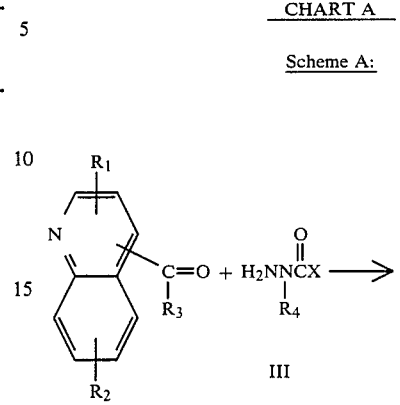

Scheme B:

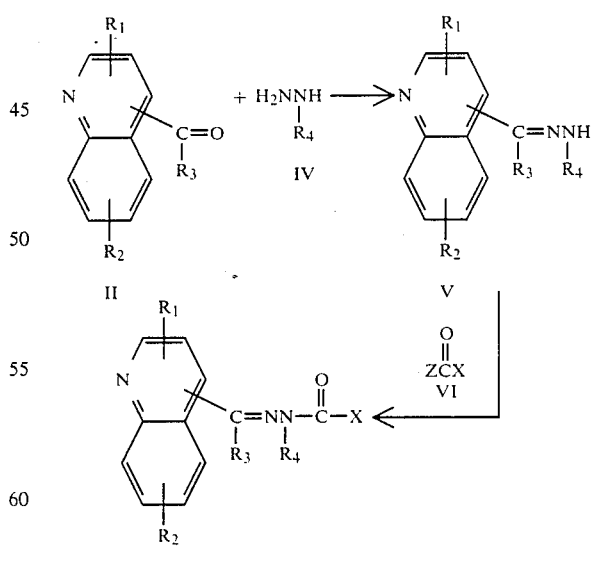

z is a halogen atom or other active group, for example, an anhydride.

Scheme C:

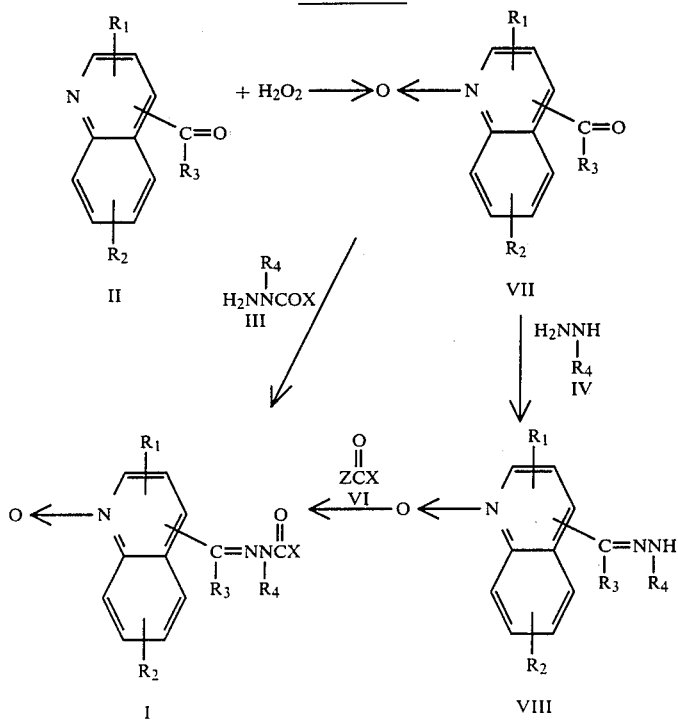

FORMULA I

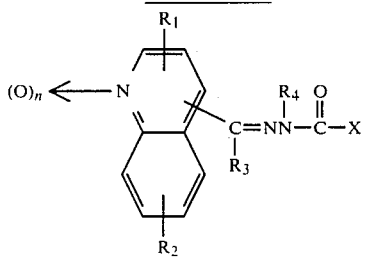

We claim:
1. A method of killing parasitic worms in humans and valuable warm-blooded domestic animals which comprises administering to humans or valuable warm-blooded domestic animals in need, a therapeutic or prophylactic dosage of a quinolinyl acylhydrazone, hydrate thereof or pharmaceutically acceptable salt thereof of the formula:

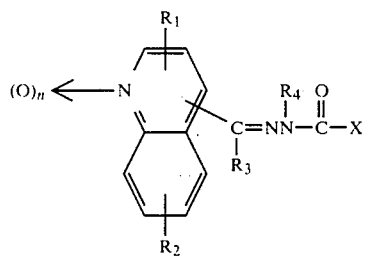

wherein X is (a) hydrogen; (b) $C_1-C_{10}$ alkyl; (c) $C_2-C_6$ alkenyl; (d) $C_2-C_6$ alkynyl; (e) cyclo($C_3-C_{10}$)alkyl optionally substituted with one, 2 or 3 $C_1-C_4$ alkyl, $C_2-C_4$ alkenyl, $C_1-C_4$ alkoxy, trifluoromethyl, or halo; (f) pyrrolidinyl; (g) piperidinyl; (h) 1-methylpyrrolidinyl; (i) 1-methylpiperidinyl; (j) $C_2-C_6$ alkoxyalkyl; (k) cyclo($C_3-C_{10}$)alkyl($C_1-C_4$)alkyl; (m) phenoxy($C_1-C_4$)alkyl optionally substituted with one, 2 or 3 $C_1-C_4$ alkyl, $C_1-C_4$ alkoxy, halo, or trifluoromethyl; (n) uredio($C_1-C_4$)alkyl; (o) $C_2-C_6$ alkoxy; (p) diphenylmethoxy; (s) benzyloxy optionally substituted with one, 2 or 3 $C_1-C_4$ alkyl, $C_1-C_4$ alkoxy, halo, or trifluoromethyl; (t) heteroaromatic optionally substituted with one, 2 or 3 $C_1-C_4$ alkyl, $C_1-C_3$ alkoxy, halo, $C_1-C_3$ alkylthio, or trifluoromethyl; (u) phenyl optionally substituted with one, 2 or 3 $C_1-C_4$ alkyl, halo, hydroxy, trifluoromethyl, $C_2-C_6$ dialkylamino, $C_1-C_3$ alkylthio or nitro; or (v) phenyl optionally substituted with the divalent $C_1-C_2$ alkylenedioxy;

wherein $R_1$ and $R_2$, being the same or different, are hydrogen; hydroxy; $C_1-C_4$ alkyl; $C_1-C_3$ alkoxy; $C_1-C_3$ alkylthio; halo or trifluoromethyl;

wherein $R_3$ is hydrogen; $C_1-C_4$ alkyl; cyclo($C_3-C_6$)alkyl optionally substituted with one, 2 or 3 $C_1-C_3$ alkyl; phenyl optionally substituted with one, 2 or 3 $C_1-C_4$ alkyl, halo, trifluoromethyl, or $C_1-C_3$ alkoxy; phenyl($C_1-C_3$)alkyl optionally substituted with one, 2 or 3 $C_1-C_4$ alkyl, halo, trifluoromethyl, or $C_1-C_3$ alkoxy; or 1,3-dioxacyclohexan-5-yl;

wherein $R_4$ is hydrogen; $C_1-C_2$ alkyl; cyclo($C_3-C_6$)alkyl optionally substituted with one, 2 or 3 $C_1-C_3$ alkyl; phenyl optionally substituted with one, 2 or 3 $C_1-C_4$ alkyl, halo, trifluoromethyl, or $C_1-C_3$ alkoxy; phenyl($C_1-C_3$)alkyl optionally substituted with one, 2 or 3 $C_1-C_4$ alkyl, halo, trifluoromethyl, or $C_1-C_3$ alkoxy;

wherein n is zero or one;

with the proviso that $R_1$, $R_2$, and $R_3$ are each hydrogen and X is 4-(1,1-dimethylethyl)phenyl only when the compound is not a 2- or 3- quinolinyl acylhydrazone;

with the proviso that $R_1$, $R_2$ and $R_3$ are each hydrogen and X is hydrogen or methyl only when the compound is not a 4-quinolinyl; and X is 2-methylphenyl only when the compound is not a 3-quinolinyl.

2. The method according to claim 1 wherein the compound, hydrate or pharmaceutically acceptable salt thereof is a 4-quinolinyl acylhydrazone or a 3-quinolinyl acylhydrazone.

3. The method according to claim 1 wherein the compound, hydrate or pharmaceutically acceptable salt thereof is a 4-quinolinyl acylhydrazone.

4. The method according to claim 1 wherein X is phenyl, 3-methylphenyl, ethoxy or nicotinyl.

5. The method according to claim 1 wherein X is phenyl, ethoxy or nicotinyl.

6. The method according to claim 1 wherein $R_1$ and $R_2$ are selected from the group consisting of hydrogen, methyl or a chloro atom.

7. The method according to claim 1 wherein $R_3$ and $R_4$ are selected from the group consisting of hydrogen or methyl.

8. The method according to claim 1 wherein the compound, hydrate or pharmaceutically acceptable salt thereof is selected from the group consisting of:

3-methylbenzoic acid (2-quinolinylmethylene)hydrazide ethyl (4-quinolinylmethylene)carbazate;

nicotinic acid (2-quinolinylmethylene)hydrazide hydrate;

benzoic acid (4-quinolinylmethylene)hydrazide;

2-thiophenecarboxylic acid (4-quinolinylmethylene)hydrazide;

cyclobutanecarboxylic acid (4-quinolinylmethylene)hydrazide;

propanoic acid (3-quinolinylmethylene)hydrazide;

cyclohexanecarboxylic acid (3-quinolinylmethylene)hydrazide;

acetic acid (3-quinolinylmethylene)hydrazide;

9. A compound, hydrate thereof or pharmaceutically acceptable salt thereof of the formula

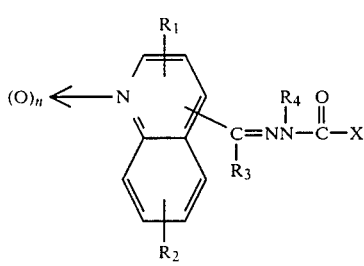

I wherein X is (a) hydrogen; (b) $C_1$-$C_{10}$ alkyl; (c) $C_2$-$C_6$ alkenyl; (d) $C_2$-$C_6$ alkynyl; (e) cyclo($C_3$-$C_{10}$)alkyl optionally substituted with one, 2 or 3 $C_1$-$C_4$ alkyl, $C_2$-$C_4$ alkenyl, $C_1$-$C_4$ alkoxy, trifluoromethyl, or halo; (f) pyrrolidinyl; (g) piperidinyl; (h) 1-methylpyrrolidinyl; (i) 1-methylpiperidinyl; (j) $C_2$-$C_6$ alkoxyalkyl; (k) cyclo($C_3$-$C_{10}$)alkyl($C_1$-$C_4$)alkyl; (m) phenoxy($C_1$-$C_4$)alkyl optionally substituted with one, 2 or 3 $C_1$-$C_4$ alkyl, $C_1$-$C_4$ alkoxy, halo, or trifluoromethyl; (n) uredio($C_1$-$C_4$)alkyl; (o) $C_2$-$C_6$ alkoxy; (p) diphenylmethoxy; (r) phenoxy optionally substituted with one, 2 or 3 $C_1$-$C_4$ alkyl, $C_1$-$C_4$ alkoxy, halo, or trifluoromethyl; (s) benzyloxy optionally substituted with one, 2 or 3 $C_1$-$C_4$ alkyl, $C_1$-$C_4$ alkoxy, halo, or trifluoromethyl; (t) heteroaromatic optionally substituted with one, 2 or 3 $C_1$-$C_4$ alkyl, $C_1$-$C_3$ alkoxy, halo, $C_1$-$C_3$ alkylthio, or trifluoromethyl; (u) phenyl optionally substituted with one, 2 or 3 $C_1$-$C_4$ alkyl, halo, hydroxy, trifluoromethyl, $C_2$-$C_6$ dialkylamino, $C_1$-$C_3$ alkylthio, or nitro; or (v) phenyl optionally substituted with the divalent $C_1$-$C_2$ alkylenedioxy;

wherein $R_1$ and $R_2$, being the same or different, are hydrogen; hydroxy; $C_1$-$C_4$ alkyl; $C_1$-$C_3$ alkoxy; $C_1$-$C_3$ alkylthio; halo or trifluoromethyl;

wherein $R_3$ is hydrogen; $C_1$-$C_4$ alkyl; cyclo($C_3$-$C_6$)alkyl optionally substituted with one, 2 or 3 $C_1$-$C_3$ alkyl; phenyl optionally substituted with one, 2 or 3 $C_1$-$C_4$ alkyl, halo, trifluoromethyl, or $C_1$-$C_3$ alkoxy; phenyl($C_1$-$C_3$)alkyl optionally substituted with one, 2 or 3 $C_1$-$C_4$ alkyl, halo, trifluoromethyl, or $C_1$-$C_3$ alkoxy; or 1,3dioxacyclohexan-5-yl;

wherein $R_4$ is hydrogen; $C_1$-$C_2$ alkyl; cyclo($C_3$-$C_6$)alkyl optionally substituted with one, 2 or 3 $C_1$-$C_3$ alkyl; phenyl optionally substituted with one, 2 or 3 $C_1$-$C_4$ alkyl, halo, trifluoromethyl, or $C_1$-$C_3$ alkoxy; phenyl($C_1$-$C_3$)alkyl optionally substituted with one, 2 or 3 $C_1$-$C_4$ alkyl, halo, trifluoromethyl, or $C_1$-$C_3$ alkoxy;

wherein n is zero or one;

with the proviso that $R_1$, $R_2$, and $R_3$ are each hydrogen and X is 4-(1,1-dimethylethyl)phenyl only when the compound is not a 2- or 3- quinolinyl acylhydrazone;

with the proviso that $R_1$, $R_2$ and $R_3$ are each hydrogen and X is hydrogen or methyl only when the compound is not a 4-quinolinyl; and X is 2-methylphenyl only when the compound is not a 3-quinolinyl;

and with the further overall proviso that the compound is other than:

benzoic acid (2-quinolinylmethylene)hydrazide,
benzoic acid (4-quinolinylmethylene)hydrazide,
acetic acid (2-quinolinylmethylene)hydrazide,
acetic acid (4-quinolinylmethylene)hydrazide,
isonicotinic acid (4-quinolinylmethylene)hydrazide,
isonicotinic acid (2-quinolinylmethylene)hydrazide,
2,4,5-trichlorophenoxyacetic acid (2-quinolinylmethylene)hydrazide,
2,4-dichlorophenoxyacetic acid (2-quinolinylmethylene)hydrazide,
4-chlorophenoxyacetic acid (2-quinolinylmethylene)hydrazide, and
2-hydroxy-4-bromobenzoic acid (8-hydroxy-2-quinolinylmethylene)hydrazide.

10. A compound, hydrate or pharmaceutically acceptable salt thereof according to claim 9 wherein X is selected from phenyl, ethoxy or nicotinyl.

11. A compound, hydrate or pharmaceutically acceptable salt thereof, according to claim 9 wherein the compound is a 3- or 4-quinolinyl acylhydrazone.

12. A compound, hydrate or pharmaceutically acceptable salt thereof, according to claim 9 wherein $R_1$ and $R_2$ are selected from the group consisting of hydrogen, methyl or a chloro atom.

13. A compound, hydrate or a pharmaceutically acceptable salt thereof, according to claim 9 wherein $R_3$ and $R_4$ are selected from the group consisting of hydrogen or methyl.

14. A compound, hydrate or pharmaceutically acceptable salt thereof, according to claim 9 selected from the group consisting of
3-methylbenzoic acid (2-quinolinylmethylene)hydrazide;
ethyl (4-quinolinylmethylene)carbazate;
nicotinic acid (2-quinolinylmethylene)hydrazide hydrate;
2-thiophenecarboxylic acid (4-quinolinylmethylene)hydrazide;
cyclobutanecarboxylic acid (4-quinolinylmethylene)hydrazide;
propanoic acid (3-quinolinylmethylene)hydrazide;
cyclohexanecarboxylic acid (3-quinolinylmethylene)hydrazide;
acetic acid (3-quinolinylmethylene)hydrazide;

15. An anthelmintic composition for administration to animals comprising a physiologically acceptable carrier and adjuvants, and at least an effective anthelmintic amount of a quinolinyl acylhydrazone, hydrate or pharmaceutically acceptable salt thereof of the formula:

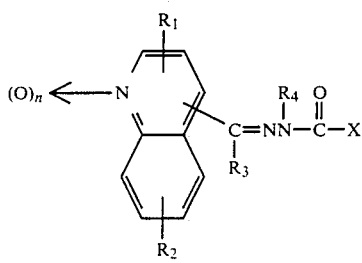

wherein X is (a) hydrogen; (b) $C_1$-$C_{10}$ alkyl; (c) $C_2$-$C_6$ alkenyl; (d) $C_2$-$C_6$ alkynyl; (e) cyclo($C_3$-$C_{10}$)alkyl optionally substituted with one, 2 or 3 $C_1$-$C_4$ alkyl, $C_2$-$C_4$ alkenyl, $C_1$-$C_4$ alkoxy, trifluoromethyl, or halo; (f) pyrrolidinyl; (g) piperidinyl; (h) 1-methylpyrrolidinyl; (i) 1-methylpiperidinyl; (j) $C_2$-$C_6$ alkoxyalkyl; (k) cyclo($C_3$-$C_{10}$)alkyl($C_1$-$C_4$)alkyl; (m) phenoxy($C_1$-$C_4$)alkyl optionally substituted with one, 2 or 3 $C_1$-$C_4$ alkyl, $C_1$-$C_4$ alkoxy, halo, or trifluoromethyl; (n) uredio($C_1$-$C_4$)alkyl; (o) $C_2$-$C_6$ alkoxy; (p) diphenylmethoxy; (r) phenoxy optionally substituted with one, 2 or 3 $C_1$-$C_4$ alkyl, $C_1$-$C_4$ alkoxy, halo, or trifluoromethyl; (s) benzyloxy optionally substituted with one, 2 or 3 $C_1$-$C_4$ alkyl, $C_1$-$C_4$ alkoxy, halo, or trifluoromethyl; (t) heteroaromatic optionally substituted with one, 2 or 3 $C_1$-$C_4$ alkyl, $C_1$-$C_3$ alkoxy, halo, $C_1$-$C_3$ alkylthio, or trifluoromethyl; (u) phenyl optionally substituted with one, 2 or 3 $C_1$-$C_4$ alkyl, halo, hydroxy, trifluoromethyl, $C_2$-$C_6$ dialkylamino, $C_1$-$C_3$ alkylthio, or nitro; or (v) phenyl optionally substituted with the divalent $C_1$-$C_2$ alkylenedioxy;

wherein $R_1$ and $R_2$, being the same or different, are hydrogen; hydroxy; $C_1$-$C_4$ alkyl; $C_1$-$C_3$ alkoxy; $C_1$-$C_3$ alkylthio; halo or trifluoromethyl;

wherein $R_3$ is hydrogen; $C_1$-$C_4$ alkyl; cyclo($C_3$-$C_6$)alkyl optionally substituted with one, 2 or 3 $C_1$-$C_3$ alkyl; phenyl optionally substituted with one, 2 or 3 $C_1$-$C_4$ alkyl, halo, trifluoromethyl, or $C_1$-$C_3$ alkoxy; phenyl($C_1$-$C_3$)alkyl optionally substituted with one, 2 or 3 $C_1$-$C_4$ alkyl, halo, trifluoromethyl, or $C_1$-$C_3$ alkoxy; or 1,3-dioxacyclohexan-5-yl;

wherein $R_4$ is hydrogen; $C_1$-$C_2$ alkyl; cyclo($C_3$-$C_6$)alkyl optionally substituted with one, 2 or 3 $C_1$-$C_3$ alkyl; phenyl optionally substituted with one, 2 or 3 $C_1$-$C_4$ alkyl, halo, trifluoromethyl, or $C_1$-$C_3$ alkoxy; phenyl($C_1$$C_3$)alkyl optionally substituted with one, 2 or 3 $C_1$-$C_4$ alkyl, halo, trifluoromethyl, or $C_1$-$C_3$ alkoxy;

wherein n is zero or one;

with the proviso that $R_1$, $R_2$, and $R_3$ are each hydrogen and X is 4-(1,1-dimethylethyl)phenyl only when the compound is not a 2- or 3- quinolinyl acylhydrazone;

with the proviso that $R_1$, $R_2$ and $R_3$ are each hydrogen and X is hydrogen or methyl only when the compound is not a 4-quinolinyl; and X is 2-methylphenyl only when the compound is not a 3-quinolinyl.

16. The composition of claim 15 in which the compound, hydrate or pharmaceutically acceptable salt thereof is selected from the group consisting of
3-methylbenzoic acid (2-quinolinylmethylene)hydrazide;
ethyl (4-quinolinylmethylene)carbazate;
nicotinic acid (2-quinolinylmethylene)hydrazide hydrate;
benzoic acid (4-quinolinylmethylene)hydrazide;
2-thiophenecarboxylic acid (4-quinolinylmethylene)hydrazide;
cyclobutanecarboxylic acid (4-quinolinylmethylene)hydrazide;
propanoic acid (3-quinolinylmethylene)hydrazide;
cyclohexanecarboxylic acid (3-quinolinylmethylene)hydrazide;
acetic acid (3-quinolinylmethylene)hydrazide;

17. The composition of claim 15 in which the compound, hydrate or pharmaceutically acceptable salt thereof is selected from the group consisting of
3-methylbenzoic acid (2-quinolinylmethylene)hydrazide;
ethyl (4-quinolinylmethylene)carbazate;
nicotinic acid (2-quinolinylmethylene)hydrazide hydrate;
2-thiophenecarboxylic acid (4-quinolinylmethylene)hydrazide;
cyclobutanecarboxylic acid (4-quinolinylmethylene)hydrazide;
propanoic acid (3-quinolinylmethylene)hydrazide;
cyclohexanecarboxylic acid (3-quinolinylmethylene)hydrazide;
acetic acid (3-quinolinylmethylene)hydrazide;

18. A compound, hydrate or pharmaceutically acceptable salt thereof, according to claim 9 wherein the compound is a 4-quinolinyl acylhydrazone.

19. The compound according to claim 9 wherein $R_1$, $R_2$, $R_3$ and $R_4$ are all hydrogen, X is ethyl and n is 0; namely propanoic acid (3-quinolinylmethylene)hydrazide.

* * * * *